(12) United States Patent
Woodrow

(10) Patent No.: US 6,949,509 B2
(45) Date of Patent: Sep. 27, 2005

(54) PHARMACEUTICAL COMPOSITION CONTAINING A SMALL OR MEDIUM SIZE PEPTIDE

(75) Inventor: Wayne Woodrow, Toronto (CA)

(73) Assignee: Patents Exploitation Company B.V., Amsterdam (NL)

(*) Notice: Subject to any disclaimer, the term of this patent is extended or adjusted under 35 U.S.C. 154(b) by 93 days.

(21) Appl. No.: 09/776,266

(22) Filed: Feb. 2, 2001

(65) Prior Publication Data

US 2001/0027177 A1 Oct. 4, 2001

(30) Foreign Application Priority Data

Feb. 4, 2000 (EP) .............................. 00102429

(51) Int. Cl.⁷ .............................................. A61K 38/00
(52) U.S. Cl. ......................................................... 514/9
(58) Field of Search ...................... 514/9, 15

(56) References Cited

U.S. PATENT DOCUMENTS 4,853,375 A * 8/1989 Krupin et al. .............. 514/152
5,482,931 A * 1/1996 Harris et al. ................. 514/15
5,763,398 A * 6/1998 Bengtsson .................. 514/11
5,783,559 A * 7/1998 Florin-Robertsson et al. . 514/12

FOREIGN PATENT DOCUMENTS

WO   WO9501183   1/1995   .......... A61K/37/34

OTHER PUBLICATIONS

Fredholt et. al. Alpha–chymotrypsin–catalyzed degradation of desmopressin (dDAVP): influence of pH, concentration and various cyclodextrins. Int J Pharm Feb. 15, 1999; 178(2): 223–9.*

"Martindale's Complete Drug Reference", *Pharmaceutical Press*, 1999, pp. 735–736.

Clayton Petty M.D., and Nelson L. Cunningham, M.D., "Insulin Adsorption by Glass Infusion Bottles, Polyvinylchloride Infusion Containers, and Intravenous Tubing", *Anesthesiology*, vol. 40, No. 4, (1974).

A.T. Florence and D. Attwood, *Physicochemical Principles of Pharmacy*, Third Edition, pp. 328–331, (1999).

* cited by examiner

Primary Examiner—Christopher R. Tate
Assistant Examiner—Maury Audet
(74) Attorney, Agent, or Firm—Abelman, Frayne & Schwab

(57) ABSTRACT

Pharmaceutical compositions containing a small or medium size peptide, free from preservatives and stable before and during the use.

28 Claims, No Drawings

PHARMACEUTICAL COMPOSITION CONTAINING A SMALL OR MEDIUM SIZE PEPTIDE

CROSS-REFERENCE TO RELATED APPLICATIONS

This application claims priority from EP 00 102 429.8 filed on Feb. 4, 2000, which is hereby incorporated by reference.

FIELD OF THE INVENTION

The present invention relates to a pharmaceutical composition containing a small or medium size peptide, preferably a small or medium size cyclic peptide, free from preservatives and anyway stable before and during the use.

STATE OF THE ART

A remarkable number of peptides, derivatives and analogues thereof are known in therapy. They are often endowed with an utterly powerful biologic activity, therefore only very small amounts are required for therapeutic goals. Among these, small and medium size peptides, preferably small or medium size cyclic peptides, more preferably those containing one or more sulfur atoms within the cyclus, and most preferably those containing at least two sulfur atoms within the cyclus, such as, for example, analogues and derivatives of oxitocin and vasopressin, such as desmopressin (termed 1-deamino-8-D-arginin-vasopressin or 1-(3-mercaptopropanoic acid)-8-D-argininevasopressin), a powerful antidiuretic useful in the treatment of urinary disorders associated to, for example, insipidus diabetes and nocturnal enuresis.

One of the problems arising with peptide drugs, especially those containing easily oxidizable sulfur bonds or sulfur bridges, is the easy degradation of their aqueous solutions.

A further problem often encountered with the preparation of pharmaceutically acceptable solutions of small and medium size peptides is a seeming loss of titre in time which is due to ongoing adsorption of the peptide drug on the surface of the container material, thus entailing a considerable loss of potency and/or activity of the pharmaceutical composition. Such adsorption problem of peptide drugs is well-known in the pharmaceutical arts. For example, calcitonin may be quickly adsorbed onto the plastic of intravenous giving sets such that addition of a protein as a "preservative" (acting as an adsorption inhibitor) is required (Martindale's "Complete Drug Reference", Pharmaceutical Press, 1999, pp.735–736). As far as e.g. insulin is concerned, it has been reported by C. Petty and N. L. Cunningham (*Anaesthesiology* 40, 400, 1974, recently reviewed by A. T. Florence and D. Attwood in "Physicochemical Principles of Pharmacy", third edition, pp. 328–331) that losses of as many as 78.8% of activity/potency may occur because of adsorption of insulin to glass bottles and plastic tubing used in giving sets. Accordingly, many preservatives able of inhibiting adsorption of peptide drugs onto container materials have been investigated. For example, the patent application WO 95/01185 (in the name of Ferring A B) claims a pharmaceutical composition for administering peptides, such as desmopressin, containing a buffer, a quaternary amine as preservative or disinfectant, and an agent for controlling the osmotic pressure. Besides the preservative or disinfectant activity already cited (i.e. the prevention of the degradation of the active principle), the quaternary amine is capable of preventing the active principle to be adsorbed by the walls of the composition container, especially when these walls are of polymeric material. In fact, Example 5 shows that desmopressin solutions free from preservative lose about the half of active principle because of the adsorption by the walls of polystyrene, polypropylene and glass tubes, after 24 hours at room temperature. The preferred quaternary amine according to WO 95/01185 is benzalkonium chloride. Recently, Hofmann T. et al., Springer-Verlag, 1998, 46:146–151 reported that this preservative causes the irreversible suppression of the nasal ciliar motility, such that its banning from the formulations for nasal administration is suggested.

The patent application WO 95/01183 (in the name of Ferring A B) discloses a composition for the nasal administration of desmopressin. Though claim 1 does not report the presence of specific excipients, it is apparent from the description and the examples that such composition, in particular the "long shelf life composition" always contains a preservative such as chlorobutanol or benzalkonium chloride.

SUMMARY OF THE INVENTION

It has been now surprisingly found that pharmaceutical compositions containing a small or medium size peptide and which are free from preservatives not only are suitably stable (as far as degradation is concerned), likewise analogous compositions containing this kind of additive, but also do not show the problem of the adsorption of the active principle by the walls of the container, envisaged by the prior art.

DESCRIPTION OF THE INVENTION

The present invention relates to pharmaceutical compositions containing a therapeutically effective amount of a small or medium size peptide or of pharmaceutically acceptable derivatives thereof in aqueous solution, characterized in that they are free from preservatives. In particular, the pharmaceutical compositions of the invention, unlike test compositions prepared for clinical trials or for short term potency investigations on laboratory scale, are intended as marketable, ready-to-use products exhibiting an extended shelf life, even at room temperature.

The term "preservatives", in the context of the present application, embraces all those additives which preserve the peptide drug's titre in the pharmaceutical solution and thus prevent losses of the solution's potency and/or activity. In particular, the term "preservatives" embraces both, degradation inhibitors (like antioxidants or antimicrobial additives) as well as adsorption inhibitors (preventing adsorption of the active principle onto container walls).

The peptide of the composition of the present invention is selected from small or medium size peptides, preferably from small or medium size cyclic peptides, more preferably from small or medium size cyclic peptides containing one or more sulfur atoms within the cyclus, and most preferably from small or medium size cyclic peptides containing at least two sulfur atoms within the cyclus, and the pharmaceutically acceptable derivatives (like e.g. salts or esters) thereof. The most preferred peptides of the composition of the present invention are selected from the group consisting of derivatives and analogues of oxytocin and vasopressin such, as, for example, terlipressin [(N-α-triglycin-8-lysin)-vasopressin], carbetocin [(1-desamino-1monocarba-2(O-methyl)tyrosine)-oxitocin], and desmopressin (1-deamino-8-D-arginin-vasopressin or 1-(3-mercaptopropanoic acid)-

8-D-argininevasopressin), and the salts thereof. Among the foregoing most preferred peptides, particularly preferred for the aim of the present invention are the vasopressin analogues, more in particular those analogues containing a mercaptopropanyl radical, desmopressin acetate hydrate being the most preferred.

In a preferred embodiment, the composition of the present invention has a pH comprised between 3.5 and 6. For maintaining such a pH value the composition shall contain a suitable buffer such as, for example, citric acid/disodium phosphate dihydrate or citric acid/trisodium citrate dihydrate.

The composition of the present invention may also contain an agent for controlling the osmolarity such as, for example, sodium chloride.

In a preferred embodiment, the composition of the invention contains at least 0.02 mg of desmopressin, at least 3 mg of a buffer, an amount of agent for controlling the osmolarity such as the osmolarity is maintained to the physiologic values of the human plasma, and 1 ml of purified water.

Preferably the composition of the present invention contains from 3 to 6 mg of the citric acid/disodium phosphate dihydrate buffer, or from 5 to 11 mg of the citric acid/trisodium citrate dihydrate buffer.

More preferably, the composition of the present invention contains from 0.02 to 0.15 mg of desmopressin, preferably 0.1 mg, from 1 to 2.5 mg of citric acid monohydrate, preferably 1.7 mg, from 2 to 5 mg of disodium phosphate dihydrate, preferably 3 mg, 1 ml of water and an amount of sodium chloride such that the osmolarity is kept at the physiological values of the human plasma.

The advantages provided by the composition of the present invention over the prior art compositions are apparent. The possibility of avoiding the use of preservatives has a positive rebound from the toxicological point of view as these substances—and the case of benzalkonium chloride is epitomising—are often a source of allergic and irritative reactions from the mucosae. Furthermore the present composition represents an overcoming of a prior art prejudice attesting that peptide solutions in general and desmopressin solutions in particular free from preservatives have the drawback—further to possible degradation—of suffering an adsorption process of the active principle by the container walls. As it is demonstrated below, the composition of the invention, though free from preservatives, does not show such a drawback.

The composition of the present invention is prepared in pre-sterile environment and sterilely filtered through 0,22 μm filters.

This is administered by a spray device filled in sterile environment under nitrogen. The vial of the spray device is preferably of glass or of plastic, e.g. of a polymeric material. Such device is equipped with a multidose pump of a kind allowing the prevention of the bacterial contamination of the drug solution, before and during the use, thanks to the protection of the aspiration air by an absolute filter and an auto-blocking mechanism of the actuator. An example of a spray device of this kind is that described by the patent application EP 0 815 946 (in the name of Pfeiffer GmbH Erich).

Examples of accomplishment of the present invention will be now provided.

EXAMPLE 1

| Solution at pH 5 | |
| --- | --- |
| Desmopressin acetate hydrate | 0.1 mg |
| (equal to desmopressin base) | (89 μg) |
| Citric acid monohydrate | 1.7 mg |
| Disodium phosphate dihydrate | 3.0 mg |
| Sodium chloride | 7.5 mg |
| Purified water | 1 ml |

EXAMPLE 2

| Solution at pH 4 | |
| --- | --- |
| Desmopressin acetate hydrate | 0.1 mg |
| (equal to desmopressin base) | (89 μg) |
| Citric acid monohydrate | 4.64 mg |
| Trisodium citrate dihydrate | 4.6 mg |
| Sodium chloride | 6.8 mg |
| Purified water | 1 ml |

EXAMPLE 3

Evaluation of the Adsorption of the Active Principle by the Container Walls

The compositions of Examples 1 and 2 were put in glass containers closed with a polymeric material pump, at room temperature for 4 days, and the titre in active principle was then evaluated.

The results are set forth in the following Table 1.

TABLE 1

| Composition | Titre at time zero | Titre after 4 days |
| --- | --- | --- |
| Example 1 | 108.5% | 106.9% |
| Example 2 | 103.3% | 101.5% |

The results set forth by the table above clearly show that for both the compositions the adsorption process of the active principle on the glass and the polymeric material pump is negligible.

EXAMPLE 4

Evaluation of the Adsorption of the Active Principle by the Container Walls

The compositions of Examples 1 and 2 were put in polymeric containers closed with a polymeric material pump, at room temperature for 4 days, and the titre in active principle was then evaluated.

The results are set forth in the following Table 2.

TABLE 2

| Composition | Titre at time zero | Titre after 4 days |
| --- | --- | --- |
| Example 1 | 103.6% | 101.6% |
| Example 2 | 101.1% | 101.1% |

The results set forth by the table above clearly show that for both the compositions the adsorption process of the active principle on the polymeric material of both, container and pump is negligible.

EXAMPLE 5

Stability Test

The quality attributes required for the compositions of the present invention are the following:

| Parameter | Attribute |
| --- | --- |
| PH | 3.5–6.0 |
| Desmopressin acetate hydrate | 90–110 µg/ml |
| Microbiological quality | Sterile |

The compositions of the present invention were evaluated by stability tests in type I glass vials equipped with dispenser pump.

The applied test protocols were the following:

Real time Test

It was carried out at a temperature of 5° C.±3° C. according to the scheme of Table 3.

TABLE 3

| Test | Beginning | 3 months | 6 months | 12 months | 18 months |
| --- | --- | --- | --- | --- | --- |
| PH | X | X | X | X | X |
| Desmopressin Acetate hydrate | X | X | X | X | X |
| Microbiological quality | X | — | — | — | X |

The results are set forth in the following Tables 4 and 5

TABLE 4

(composition of Example 1)

| Test | Beginning | 3 months | 6 months | 12 months | 18 months |
| --- | --- | --- | --- | --- | --- |
| PH | 5.12 | 5.16 | 5.14 | 5.10 | 5.15 |
| Desmopressin Acetate hydrate | 108.3% | 107.6% | 106.4% | 107.1% | 104.7% |
| Microbiological quality | Sterile | — | — | — | Sterile |

TABLE 5

(composition of Example 2)

| Test | Beginning | 3 months | 6 months | 12 months | 18 months |
| --- | --- | --- | --- | --- | --- |
| PH | 4.00 | 4.00 | 4.00 | 3.98 | 4.02 |
| Desmopressin Acetate hydrate | 109.0% | 108.1% | 108.8% | 107.7% | 106.0% |
| Microbiological quality | Sterile | — | — | — | Sterile |

Room Temperature Tests

They were carried out at a temperature of 25° C.±2° C. and 60%±5% of relative humidity according to the scheme of Table 6

TABLE 6

| Test | Beginning | 3 months | 6 months | 12 months | 18 months |
| --- | --- | --- | --- | --- | --- |
| PH | X | X | X | X | X |
| Desmopressin Acetate hydrate | X | X | X | X | X |
| Microbiological quality | X | — | — | — | X |

The results were set forth in the following Tables 7 and 8.

TABLE 7

(composition of Example 1)

| Test | Beginning | 3 months | 6 months | 12 months | 18 months |
| --- | --- | --- | --- | --- | --- |
| PH | 5.12 | 5.16 | 5.12 | 5.10 | 5.08 |
| Desmopressin Acetate hydrate | 108.3% | 104.4% | 100.8% | 98.9% | 93.0% |
| Microbiological quality | Sterile | — | — | — | Sterile |

TABLE 8

(composition of Example 2)

| Test | Beginning | 3 months | 6 months | 12 months | 18 months |
| --- | --- | --- | --- | --- | --- |
| PH | 4.00 | 3.98 | 3.98 | 3.95 | 3.97 |
| Desmopressin Acetate hydrate | 109.0% | 105.8% | 100.1% | 96.9% | 92.5% |
| Microbiological quality | Sterile | — | — | — | Sterile |

The results of the tables above show how the compositions of the present invention, though free from the preservatives deemed necessary by the prior art, anyway reveal to be stable in that concerns the active principle both at low temperature (5° C.) and at room temperature (25° C.).

What is claimed is:

1. A pharmaceutical composition stable for at least 18 months at room temperature which comprises a therapeutically effective amount of a peptide or of a pharmaceutically acceptable derivative thereof selected from the group consisting of derivatives and analogues of oxytocin and vasopressin and the salts thereof and further containing a buffer in aqueous solution, wherein the composition has a pH between 3.5 and 6, wherein the composition is free from preservatives selected from the group consisting of adsorption inhibitors which inhibit adsorption of the peptide onto a container's walls and degradation inhibitors selected from the group consisting of antioxidants and antimicrobial additives.

2. A pharmaceutical composition stable for at least 18 months at room temperature consisting of a therapeutically effective amount of a peptide or of a pharmaceutically acceptable derivative thereof selected from the group consisting of derivatives and analogues of oxytocin and vasopressin and the salts thereof and of a buffer in aqueous solution, wherein the composition has a pH comprised between 3.5 and 6, wherein the composition is free from preservatives selected from the group consisting of adsorption inhibitors which inhibit adsorption of the peptide onto container's walls and degradation inhibitors selected from the group consisting of antioxidants and antimicrobial inhibitors.

3. The stable pharmaceutical composition according to claim 1, wherein the peptide is selected from the group consisting of the analogues of vasopressin, and the salts thereof.

4. The pharmaceutical composition according to claim 2, wherein the peptide is selected from the group consisting of the analogues of vasopressin, and the salts thereof.

5. The pharmaceutical composition according to claim 3, wherein the analogue of vasopressin contains a mercaptopropanoyl radical.

6. The pharmaceutical composition according to claim 4, wherein the analogue of vasopressin contains a mercaptopropanoyl radical.

7. The pharmaceutical composition according to claim 5, wherein the analogue of vasopressin is desmopressin acetate hydrate.

8. The pharmaceutical composition according to claim 6, wherein the analogue of vasopressin is desmopressin acetate hydrate.

9. The pharmaceutical composition according to claim 1, wherein the buffer is selected from the group consisting of citric acid/disodium phosphate dihydrate and citric acid/trisodium citrate dihydrate.

10. The pharmaceutical composition according to claim 2, wherein the buffer is selected from the group consisting of citric acid/disodium phosphate dihydrate and citric acid/trisodium citrate dihydrate.

11. The pharmaceutical composition according to claim 1, containing an agent for controlling the osmolarity.

12. The pharmaceutical composition according to claim 2, further containing an agent for controlling the osmolarity.

13. The pharmaceutical composition according to claim 11, wherein the agent for controlling the osmolarity is sodium chloride.

14. The pharmaceutical composition according to claim 12, wherein the agent for controlling the osmolarity is sodium chloride.

15. The pharmaceutical composition according to claim 1, containing at least 0.02 mg of desmopressin, at least 3 mg of the buffer, and an amount of an agent for controlling the osmolarity such that the osmolarity is kept at the physiologic values of the human plasma, and 1 ml of purified water.

16. The pharmaceutical composition according to claim 2, containing at least 0.02 mg of desmopressin, and containing at least 3 mg of the buffer, and further containing an amount of an agent for controlling the osmolarity such that the osmolarity is kept at the physiologic values of the human plasma, in 1 ml of purified water.

17. The pharmaceutical composition according to claim 9, containing from 3 to 6 mg of citric acid/disodium phosphate dihydrate buffer, or from 5 to 11 mg of citric acid/trisodium citrate dihydrate buffer.

18. The pharmaceutical composition according to claim 15, containing from 0.02 to 0.15 mg of desmopressin, from 1 to 2.5 mg of citric acid monohydrate, from 2 to 5 mg of disodium phosphate dihydrate, 1 ml of water and an amount of sodium chloride such that the osmolarity is kept at the physiologic values of the human plasma.

19. The pharmaceutical composition according to claim 18, containing 0.1 mg of desmopressin, 1.7 mg of citric acid monohydrate, 3 mg of disodium phosphate dihydrate, 1 ml of water and an amount of sodium chloride such that the osmolarity is kept at the physiologic values of the human plasma.

20. The pharmaceutical composition according to claim 10, containing from 3 to 6 mg of citric acid/disodium phosphate dihydrate buffer, or from 5 to 11 mg of citric acid/trisodium citrate dihydrate buffer.

21. The pharmaceutical composition according to claim 16, containing from 0.02 to 0.15 mg of desmopressin, from 1 to 2.5 mg of citric acid monohydrate, from 2 to 5 mg of disodium phosphate dihydrate, 1 ml of water and further an amount of sodium chloride such that the osmolarity is kept at the physiologic values of the human plasma.

22. The pharmaceutical composition according to claim 18, containing 0.1 mg of desmopressin, and containing 1.7 mg of citric acid monohydrate, 3 mg of disodium phosphate dihydrate, in 1 ml of water and further an amount of sodium chloride such that the osmolarity is kept at the physiologic values of the human plasma.

23. A process for preparing the pharmaceutical composition according to claim 1, comprising operating in pre-sterile environment, sterilely filtrating through 0,22 $\mu$m filters, collecting the filtrate in sterile environment and distributing it in sterile vials.

24. A process for preparing the pharmaceutical composition according to claim 2, operating in pre-sterile environment, sterilely filtrating through 0,22 $\mu$m filters, collecting the filtrate in sterile environment and distributing it in sterile vials.

25. A spray unit containing a composition according to claim 1, and equipped with a multidose pump, absolute filter for the aspiration air, and an auto- blocking mechanism of the actuator.

26. A spray unit containing a composition according to claim 2, and equipped with a multidose pump, absolute filter for the aspiration air, and an auto-blocking mechanism of the actuator.

27. A spay unit according to claim 25, wherein the spray unit comprises a vial, wherein the vial is of glass.

28. A spay unit according to claim 25, wherein the spray unit comprises a vial, wherein the vial is of plastic.

* * * * *